United States Patent

Heiman

Patent Number: 5,759,662
Date of Patent: Jun. 2, 1998

[54] FACING FABRIC FOR REUSABLE INCONTINENT PRODUCTS

[75] Inventor: Mark J. Heiman, Mainville, Ohio

[73] Assignee: Standard Textile Co., Inc., Cincinnati, Ohio

[21] Appl. No.: 769,412

[22] Filed: Dec. 19, 1996

[51] Int. Cl.⁶ .......................... A61F 13/46; A61F 13/54; B32B 33/00
[52] U.S. Cl. .......................... 428/85; 66/194; 139/396; 428/95; 442/268; 442/288; 442/312; 442/319; 442/326; 604/378; 604/384; 604/385
[58] Field of Search .......................... 66/194; 139/396; 428/85, 95; 442/268, 288, 312, 319, 326; 604/378, 384, 385

[56] References Cited

U.S. PATENT DOCUMENTS

| | | |
|---|---|---|
| 5,065,600 | 11/1991 | Byles . |
| 5,214,942 | 6/1993 | Peake et al. . |
| 5,290,269 | 3/1994 | Heiman . |
| 5,306,536 | 4/1994 | Moretz et al. . |
| 5,330,817 | 7/1994 | Arnott et al. . |

*Primary Examiner*—James C. Cannon
*Attorney, Agent, or Firm*—Wood, Herron & Evans, L.L.P.

[57] ABSTRACT

A facing fabric (10) for a reusable incontinent product (40) having a pair of multi-filament ground yarn sets (14, 16) interknitted together with a warp knit third set of yarns (18) which define loops (22) on one face of the fabric (10) in a warp knit three bar construction. The loop-facing yarns (18) are unnapped, multi-filament polyester with a denier of about 150 to 300 denier in a range of about 1 to 5 denier per filament, and advantageously about 48 filaments when the denier is about 150 and about 132 filaments when the denier is about 300. A barrier layer (46) may be added to the fabric (10) to create the reusable incontinent product (40).

26 Claims, 2 Drawing Sheets

FACING FABRIC FOR REUSABLE INCONTINENT PRODUCTS

BACKGROUND OF THE INVENTION

I. Field of the Invention

The present invention relates to reusable incontinent products and, more particularly, to a facing fabric for such incontinent products.

II. Description of the Prior Art

Reusable incontinent products are well known and in use in a number of environments. For example, incontinent pads having a facing fabric held to a barrier layer are in use in nursing homes and hospitals and the like. These products may be cleaned and reused a number of times. Other reusable incontinent products include washable diapers and other fluid-retaining items for use on or against the body.

Many incontinent products have a facing fabric which is substantially hydrophilic (i.e., constructed of cotton or the like). Such fabrics tend to hold a significant amount of fluid against the body and thus can be uncomfortable. Other products have provided a facing fabric in which the body-facing surface is substantially hydrophobic such that fluid appearing at the interface of the body and the fabric are wicked away from the body and into the back side of the fabric. Some of these hydrophobic-based products utilize a flat weave which must be brushed or napped in order to have desired wickability characteristics. Other products utilize a loop pile construction which is desirable for a facing fabric, but due to the yarns involved, must nap or brush the surface to give it the desired hand or feel. Unfortunately, the napping damages the loops making the fabric less desirable for use as part of an incontinent product. One such fabric is shown in U.S. Pat. No. 5,330,817.

Another product which has gained considerable acceptance as a good facing fabric for reusable incontinent products is the Comply® fabric marketed by Standard Textile Co., Inc., the assignee of the present application. That facing fabric is comprised of hydrophobic upper yarns and hydrophilic lower yarns interconnected by ground yarns as described in U.S. Pat. No. 5,290,269 which is assigned to Standard Textile Co., Inc. The disclosure of said U.S. Pat. No. 5,290,269 is incorporated herein by reference. While that Comply® fabric has met with great success, the hydrophobic yarns are nonetheless brushed. Moreover, the fabric is made by a four-bar construction and also utilizes multiple yarns, both of which thus make the product relatively expensive to produce.

There is a desire to produce a less expensive facing fabric for reusable incontinent products which provides an advantageously hydrophobic body-facing surface without the drawbacks of prior facing fabrics having that characteristic.

SUMMARY OF THE INVENTION

The present invention provides a facing fabric for reusable incontinent products having a hydrophobic body-facing surface which is of relatively low cost to construct and provides a desired hand and feel with desirable wicking properties. To this end, and in accordance with the principles of the present invention, the facing fabric is knitted or woven to have a loop pile construction provided by a set of polyester, multi-filament, unnapped yarns each being about 150 to 300 denier in a range of about 1 to 5 denier per filament. The range of denier yarn may advantageously be about 150–200 denier. Where the yarn is about 150 denier, the yarn has about 48 filaments. Where the yarn is about 300 denier, the yarn has about 132 filaments. The fabric also includes ground yarns to hold the loop pile construction whereby ground yarns may also be multi-filament yarns, each being about 50 to 100 denier in a range of about 1 to 5 denier per filament.

Yarns having the denier and multi-filament characteristics above-described are relatively inexpensive and readily available, yet provide a good hand and feel and desirable wickability characteristics all without napping or brushing. Advantageously, the fabric of the present invention may be made by a three bar warp tricot knitting process which is lower in cost.

By virtue of the foregoing, there is thus provided a reusable incontinent product facing fabric which is low in cost to manufacture and yet has characteristics desirable for use in such incontinent products. The fabric may be combined with a barrier layer, for example, to form a reusable incontinent product.

These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION OF THE DRAWINGS

Figure 1:
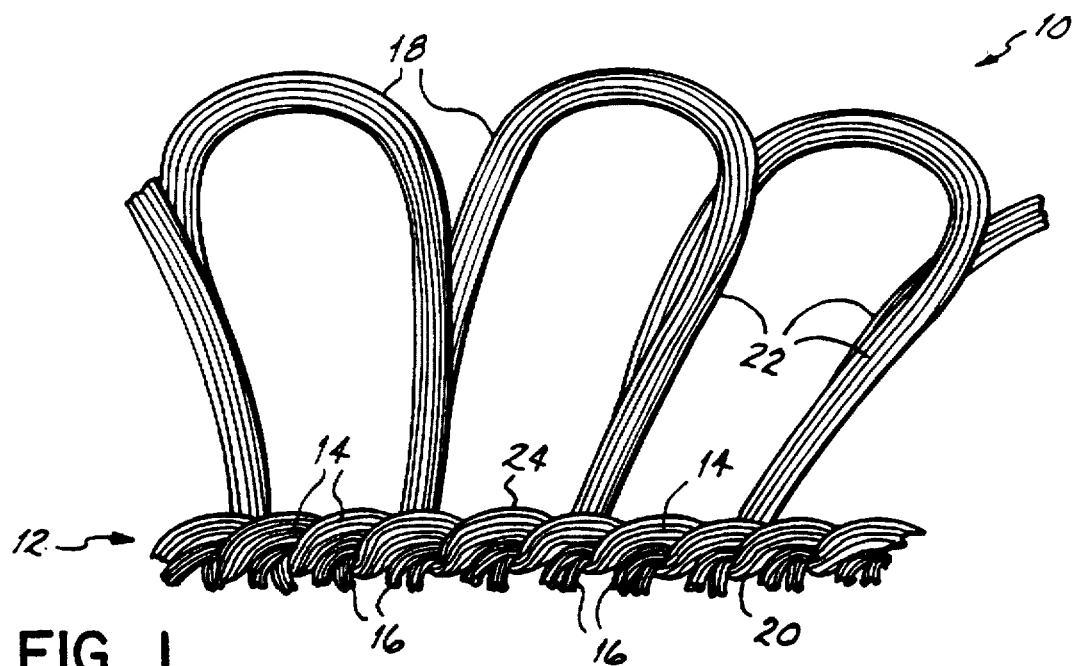
FIG. 1 is a perspective view of a facing fabric in accordance with the principles of the present invention.
Figure 2:
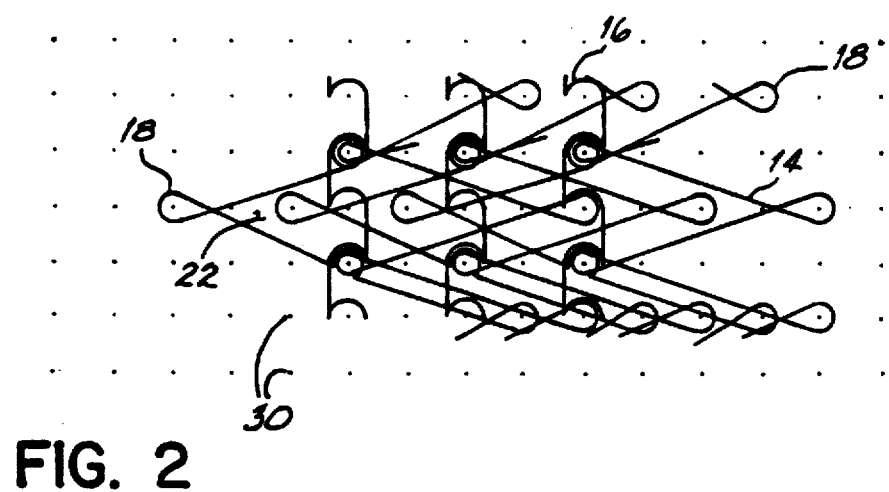
FIG. 2 is a composite diagram of the stitch pattern of the fabric of FIG. 1 as made by a three bar warp knitting machine.
Figure 3:
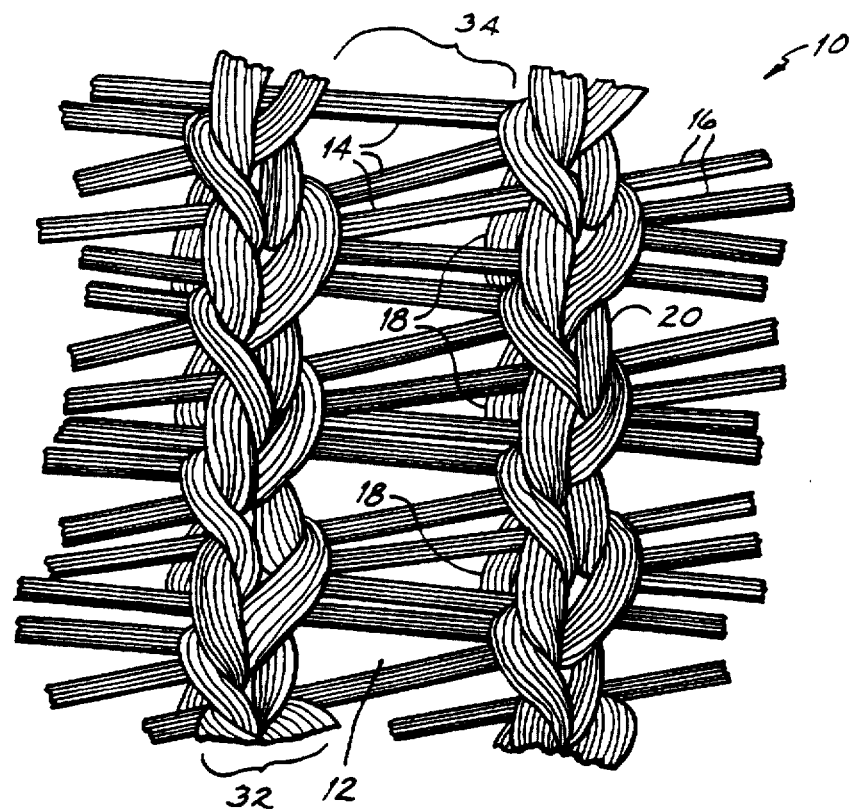
FIG. 3 is a technical back side view of the fabric of FIG. 1.

With reference to FIGS. 1–3, there is shown a facing fabric 10 constructed in accordance with the principles of the present invention. To this end, fabric 10 includes a ground layer 12 formed of a first set of ground yarns 14 and a second set of ground yarns 16 interknitted together, and a third set of yarns 18 warp-knitted in extending underlaps at a technical back 20 of fabric 10. Yarns 18 form a plurality of loops 22 extending outwardly from face 24 of the ground layer 12.

Fabric 10 is advantageously provided by a three bar warp knit construction technique. To this end, ground yarns 14 are warp knitted in a 1-0, 4-5 stitch pattern, with the second ground yarns 16 warp knitted in a 0-1, 1-0 chain stitch pattern, and the third or loop-forming yarns 18 knitted in a 1-0, 3-4, 6-7, 3-4 stitch pattern. The foregoing three bar warp knit construction is described in U.S. Pat. No. 5,214,942, the disclosure of which is incorporated herein by reference. As more fully explained in the aforementioned U.S. Pat. No. 5,214,942, the threading arrangement of the three guide bars is set up in conjunction with the stitch patterns of the three sets of yarn to deliver the ground and loop-forming yarns 14, 16, and 18 to every alternate needle 30 of the needle bar during the formation of alternate fabric courses and, then, to deliver the ground yarns 14, 16 to every alternate needle 30 of the needle bar while delivering the loop-forming yarns 18 to every intervening needle 30 during the formation of intervening fabric courses. For this purpose, the bottom yarn guide bar has every alternate guide eye threaded with a ground yarn 14 and every intervening guide eye empty, commonly referred to as a "one in, one out" threading arrangement, while the middle and top yarn guide bars have every intervening guide eye threaded with a respective ground or loop yarn 16 or 18, respectively, and every alternate guide eye empty, i.e., a "one out, one in" threading arrangement.

As may thus be seen from the foregoing, each loop 22 is formed on an empty needle 30 of one bar of three bar warp knitting equipment (not shown). The other two bars (not shown) are utilized to form the ground layer 12. The result is ribs 32 (FIG. 3) which create a channeling effect as at 34 at the technical back 20 of fabric 10. The loop pile construction which is depicted by the loops 22 at the front of fabric 10, and the channels 34 at the back thereof, are both desirable characteristics for reusable incontinent products.

In order to form a reusable incontinent product facing fabric, careful selection of the yarns is also desirable. To this end, the loop forming yarns 18 are unnapped, multi-filament, hydrophobic, synthetic yarns each being about 150 to 300 denier in a range of about 1 to 5 denier per filament. Yarns 18 may advantageously be polyester. A more advantageous range of denier for the yarns may be about 150 to 200 denier. Where the yarn has a denier of about 150, the yarn advantageously has about 48 filaments. Where further cost savings are desired, the yarn should be at the higher end of the denier range such as about 300 denier. In that case, the yarn advantageously includes about 132 filaments. Similarly, the ground yarns 14 and 16 are also multi-filament yarns each being about 50 to 100 denier in a range of about 1 to 5 denier per filament. Yarns 14 and 16 may be either a cotton\synthetic blend material, or 100% synthetic material. The synthetic material of ground yarns 14 and 16 may be polyester. A further advantage may be obtained where loop yarns 18 are texturized and are optically bright. Further, synthetic yarns 18 may be extruded in circular cross-section although other cross-sections may be employed, an example of which is a trilobal cross-section although other cross-sections will be evident to ordinarily skilled artisans. Once knitted, fabric 10 is processed in conventional manner but without napping or brushing of the loops 22.

Figure 4:
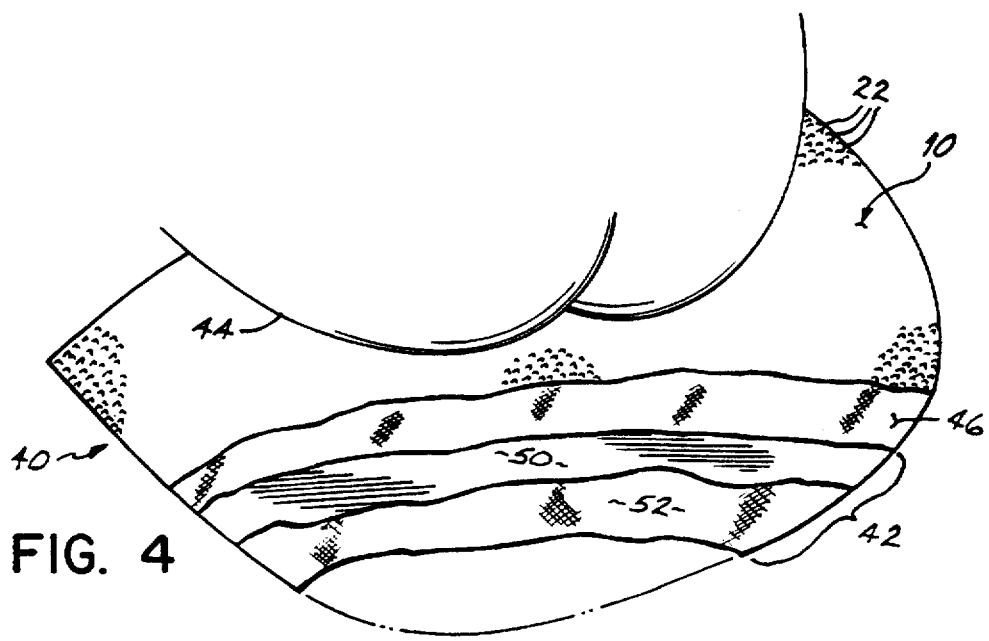
FIG. 4 is a broken-away of a reusable incontinent product made with the facing fabric of FIG. 1, with the product shown against a human body.

A reusable incontinent product 40 may be formed with fabric 10 as will now be described with reference to FIG. 4. In that figure, fabric 10 may be placed with its technical back 20 facing a barrier layer 42 such that loops 22 of fabric 10 extend outwardly away from barrier layer 42 so as to be available against the body 44 of the human (or animal) using the product. Barrier layer 42 may touch or abut fabric 10 or may be separated therefrom such as with a felt stiffener layer 46, such as where product 40 is an incontinent pad of construction comparable to that shown in the aforesaid U.S. Pat. No. 5,290,269. Layer 46 may also hold by adsorption a large quantity of the fluid (not shown) discharged from the body 44. Barrier layer 42 may be comprised of a first fluid-impervious ply 50 (such as vinyl) extruded between a tricot support ply 52 and layer 46. Felt layer 46 may in turn be stitch-quilted to fabric 10. Alternatively, felt layer 46 may be dispensed with and ply 42 secured directly to fabric 10. While product 40 is referred to herein as an incontinent pad, it will be appreciated that product 40 could alternatively be a diaper, the crotch pad of an underwear product or any other product to be held against or near a body 44 to wick and hold fluids away therefrom.

In use, fabric 10 will be utilized in reusable incontinent product 40 with the unnapped loops 22 of fabric 10 facing against the body 44. After soiling, product 40 is removed and cleaned, for example, after which product 40 may be reused.

While the present invention has been illustrated by the description of embodiments of the invention, and while the embodiments have been described in considerable detail, it is not the intention of applicants to restrict or in any way limit the scope of the appended claims to such detail. Additional advantages and modifications will readily appear to those skilled in the art. By way of example, although three bar knit construction is advantageously employed for the facing fabric of the present invention, other knit constructions, such as circular knitting, may be employed. The invention in its broader aspects is therefore not limited to the specific details, representative apparatus and methods, and illustrative examples shown and described. Accordingly, departures may be made from such details without departing from the spirit or scope of applicant's general inventive concept.

Having described the invention, what is claimed is:

1. A reusable incontinent product facing fabric comprising a plurality of yarns woven or knitted together, at least one set of the yarns defining a loop pile construction at one face of said fabric characterized in that the loop-pile set of yarns are unnapped, multi-filament polyester yarns each being about 150 to 300 denier in a range of about 1 to 5 denier per filament.

2. The reusable incontinent product facing fabric of claim 1, the loop-pile set of yarns each being about 150 to 200 denier.

3. The reusable incontinent product facing fabric of claim 1 further characterized in that the loop-pile yarns are texturized.

4. The reusable incontinent product facing fabric of claim 1 further characterized in that the loop-pile yarns are optically bright.

5. The reusable incontinent product facing fabric of claim 1 wherein said loop-pile yarns each include about 48 filaments, and are about 150 denier.

6. The reusable incontinent product facing fabric of claim 1 wherein said loop-pile yarns each include about 132 filaments, and are about 300 denier.

7. The reusable incontinent product facing fabric of claim 1 having first and second sets of ground yarns, interknitted together to define a ground, with the loop-pile yarns being loop-knitted with the ground.

8. The reusable incontinent product facing fabric of claim 7 further characterized in that the first and second sets of ground yarns are multi-filament each being about 50 to 100 denier in a range of about 1 to 5 denier per filament.

9. The reusable incontinent product facing fabric of claim 7 wherein the loop-pile yarns are knitted to the ground yarns in extended underlaps at a technical back of said fabric.

10. The reusable incontinent product facing fabric of claim 7 wherein said first ground yarns are warp knitted in a stitch pattern, said second ground yarns are wrap knitted in a chain stitch pattern, and said loop-pile set of yarns are knitted in a stitch pattern.

11. The reusable incontinent product facing fabric of claim 7 wherein said first ground yarns are warp knitted in a 1-0, 4-5 stitch pattern, said second ground yarns are warp knitted in a 0-1, 1-0 chain stitch pattern, and said loop-pile set of yarns are knitted in a 1-0, 3-4, 6-7, 3-4 stitch pattern.

12. The reusable incontinent product facing fabric of claim 1 further comprising means defining ribs in the fabric.

13. A reusable incontinent product comprising:

a facing fabric having a plurality of yarns woven or knitted together, at least one set of the yarns defining a loop pile construction at one face of said fabric characterized in that the loop-forming set of yarns are unnapped, multi-filament, polyester yarns each being about 150 to 300 denier in a range of about 1 to 5 denier per filament; and a barrier layer facing the fabric with the loop-pile of the fabric extending away from the barrier layer.

14. The reusable incontinent product of claim 13, the loop-pile set of yarns each being about 150 to 200 denier.

15. The reusable incontinent product of claim 13 further characterized in that the loop-pile yarns are texturized.

16. The reusable incontinent product of claim 13 further characterized in that the loop-pile yarns are optically bright.

17. The reusable incontinent product of claim 13 wherein said loop-pile yarns each include about 48 filaments and are about 150 denier.

18. The reusable incontinent product of claim 13 wherein said loop-pile yarns each include about 132 filaments and are about 300 denier.

19. The reusable incontinent product of claim 13 wherein the facing fabric further has first and second sets of ground yarns interknitted together to define a ground, with the loop-pile yarns being warp knitted to the ground.

20. The reusable incontinent product of claim 19 further characterized in that the first and second sets of ground yarns are multi-filament each being about 50 to 100 denier in a range of about 1 to 5 denier per filament.

21. The reusable incontinent product of claim 19 wherein the loop-pile yarns are knitted to the ground yarns in extended underlaps at a technical back of said fabric.

22. The reusable incontinent product of claim 19 wherein said first ground yarns are warp knitted in a stitch pattern, said second ground yarns are wrap knitted in a chain stitch pattern, and said loop-pile yarns are knitted in a stitch pattern.

23. The reusable incontinent product of claim 19 wherein said first ground yarns are warp knitted in a 1-0, 4-5 stitch pattern, said second ground yarns are warp knitted in a 0-1, 1-0 chain stitch pattern, and said loop-pile yarns are knitted in a 1-0, 3-4, 6-7, 3-4 stitch pattern.

24. The reusable incontinent product of claim 13 further comprising means defining ribs in the fabric.

25. The reusable incontinent product of claim 13 further comprising a layer interposed between said facing fabric and said barrier layer.

26. The reusable incontinent product of claim 13 wherein the barrier layer includes a fluid impervious ply and a supporting ply.

* * * * *

UNITED STATES PATENT AND TRADEMARK OFFICE
CERTIFICATE OF CORRECTION

PATENT NO. : 5,759,662

DATED : June 2, 1998

INVENTOR(S) : Mark J. Heiman

It is certified that error appears in the above-identified patent and that said Letters Patent is hereby corrected as shown below:

Column 4 line 58 (Claim 10), delete "wrap knitted" and replace with --warp knitted--;

Column 6, line 10 (Claim 22), delete "wrap knitted" and replace with --warp knitted--.

Signed and Sealed this

Second Day of February, 1999

*Attest:*

*Attesting Officer*

*Acting Commissioner of Patents and Trademarks*